United States Patent
Yamazaki et al.

(10) Patent No.: US 12,409,128 B2
(45) Date of Patent: Sep. 9, 2025

(54) SHAMPOO COMPRISING A SILICONE BLEND AND A TERNARY SURFACTANT MIXTURE

(71) Applicant: KAO CORPORATION, Tokyo (JP)

(72) Inventors: Naoyuki Yamazaki, Sumida-ku (JP); Hiroki Fujinaga, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 559 days.

(21) Appl. No.: 17/763,876

(22) PCT Filed: Mar. 27, 2020

(86) PCT No.: PCT/JP2020/014347
§ 371 (c)(1),
(2) Date: Mar. 25, 2022

(87) PCT Pub. No.: WO2021/065047
PCT Pub. Date: Apr. 8, 2021

(65) Prior Publication Data
US 2022/0323336 A1    Oct. 13, 2022

(30) Foreign Application Priority Data

Sep. 30, 2019  (JP) ................ 2019-180420

(51) Int. Cl.
| | | |
|---|---|---|
| C11D 9/36 | (2006.01) | |
| A61K 8/41 | (2006.01) | |
| A61K 8/44 | (2006.01) | |
| A61K 8/46 | (2006.01) | |
| A61K 8/49 | (2006.01) | |
| A61K 8/60 | (2006.01) | |
| A61K 8/86 | (2006.01) | |
| A61K 8/891 | (2006.01) | |
| A61K 8/898 | (2006.01) | |
| A61Q 5/02 | (2006.01) | |

(52) U.S. Cl.
CPC ............ *A61K 8/898* (2013.01); *A61K 8/41* (2013.01); *A61K 8/442* (2013.01); *A61K 8/447* (2013.01); *A61K 8/463* (2013.01); *A61K 8/4913* (2013.01); *A61K 8/602* (2013.01); *A61K 8/86* (2013.01); *A61K 8/891* (2013.01); *A61Q 5/02* (2013.01)

(58) Field of Classification Search
CPC .... C11D 1/02; C11D 1/72; C11D 1/62; C11D 1/65; C11D 1/83; C11D 1/90; C11D 1/86; C11D 3/0094; C11D 3/373; C11D 3/3738; C11D 9/36; C11D 2111/12
See application file for complete search history.

(56) References Cited

U.S. PATENT DOCUMENTS

| | | | | |
|---|---|---|---|---|
| 2009/0041709 A1* | 2/2009 | Hoffmann | ........... | A61K 8/85 424/70.12 |
| 2009/0041711 A1* | 2/2009 | Molenda | ........... | A61Q 5/12 424/70.12 |
| 2009/0126756 A1* | 5/2009 | Syed | ........... | A61K 8/362 424/70.13 |
| 2014/0082856 A1* | 3/2014 | Goettel | ........... | A61Q 5/10 8/406 |
| 2015/0044158 A1* | 2/2015 | Farwick | ........... | A61K 8/64 562/556 |
| 2016/0235638 A1* | 8/2016 | Rose | ........... | A61K 8/891 |
| 2016/0250118 A1* | 9/2016 | Consoli | ........... | A61K 8/39 132/206 |
| 2018/0207080 A1* | 7/2018 | Loch | ........... | A61Q 5/12 |

FOREIGN PATENT DOCUMENTS

| | | |
|---|---|---|
| JP | 2012-232953 A | 11/2012 |
| JP | 2013-517337 A | 5/2013 |
| JP | 2014-528967 A | 10/2014 |

OTHER PUBLICATIONS

Extended European Search Report issued Nov. 6, 2023, in corresponding European Patent Application No. 20870761.2, 6 pages.
Anonymous: "Quaternium-80—Surfactant—SAAPedia—Surfactant Technology Platform", SAAPedia, Aug. 8, 2014, pp. 1-3, XP055875936, Retrieved from the Internet: URL:http://www.saapedia.org/en/saa/?type=detail&id=1842 [retrieved on Jan. 3, 2022].
International Search Report issued Jun. 23, 2020 in PCT/JP2020/014347 filed Mar. 27, 2020, 3 pages.
Ecologie Com. Imp. Distr., Brazil, "Salt-Free Shampoo", Mintel GNPD, 2011, pp. 1-2.
Bubchen-Werk Ewald Hermes, Germany, "Shampoo & Conditioner", Mintel GNPD, 2013, pp. 1-2.
Aba Cosmeticos, Brazil, "Low Poo Shampoo", Mintel GNPD, 2015, pp. 1-2.
Kao, USA, "Shampoo", Mintel GNPD, 2014, pp. 1-2.
Mintel: "Shampoo & Conditioner", XP055814009 (GNPD: 1916914) Date Published: Jan. 2013.
Mintel: "Shampoo", XP055814019 (GNPD 2325513) Date Published: Feb. 2014.

* cited by examiner

*Primary Examiner* — Charles I Boyer
(74) *Attorney, Agent, or Firm* — Oblon, McClelland, Maier &Neustadt, L.L.P.

(57) ABSTRACT

A detergent comprising (A) at least one selected from the group consisting of (A1) a carbobetaine type ampholytic surfactant and (A2) a nonionic surfactant, and (B) a quaternary ammonium cation-modified silicone. A mass ratio [(A)/(B)] of the component (A) to the component (B) is 0.1 or more and 1,000 or less, and the content of an anionic surfactant is 4% by mass or less.

11 Claims, No Drawings

SHAMPOO COMPRISING A SILICONE BLEND AND A TERNARY SURFACTANT MIXTURE

FIELD OF THE INVENTION

The present invention relates to a detergent.

BACKGROUND OF THE INVENTION

There is a demand for a hair cosmetic capable of reducing the time and effort in daily hair-care activities and leading a hair-care life without stress. In particular, in the field of hair detergents, in addition to the basic function of removing hair stains, research has been conducted on hair detergents having a good feeling of use, such as good lathering, and putting fingers through hair during washing and after rinsing.

In such hair detergents, ones having a cationized silicone blended therein are known. For example, JP 2013-517337 A (PTL 1) describes that a polysiloxane of a specified structure containing quaternary ammonium groups and being branched in the siloxane moiety, becomes an active ingredient capable of imparting combability, softness, detanglability of damaged and undamaged hair, sheen, and the like and discloses formulations blended in shampoos, hair rinses, conditioners, and so on.

JP 2014-528967 A (PTL 2) discloses that when a microemulsion containing, as oil phase, a polysiloxane of a specified structure containing at least one quaternary ammonium group is used for shampoos and hair rinses, the evaluations regarding wet combability, dry combability, feel, and shine are good.

SUMMARY OF THE INVENTION

The present invention relates to a detergent containing
(A) at least one selected from the group consisting of (A1) a carbobetaine type ampholytic surfactant and (A2) a nonionic surfactant, and
(B) a quaternary ammonium cation-modified silicone represented by the following general formula (1):

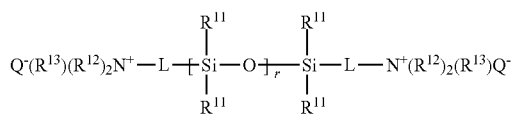

(1)

[in the formula (1), $R^{11}$ represents a hydrocarbon group having 1 or more and 6 or less carbon atoms; $R^{12}$ represents a hydrogen atom, a hydrocarbon group having 1 or more and 20 or less carbon atoms, or an amide bond-containing hydrocarbon group having 1 or more and 20 or less carbon atoms; $R^{13}$ represents a hydrocarbon group having 1 or more and 20 or less carbon atoms, or an amide bond-containing hydrocarbon group having 1 or more and 20 or less carbon atoms; L represents a divalent organic group; $Q^-$ is a counter ion of the quaternary ammonium ion; r represents a number of 2 or more; plural $R^{11}$'s and $R^{12}$'s may be the same as or different from each other; and the bonding order among the structural units within the bracket does not matter, and the bonding form may be a block form or a random form], wherein,
a mass ratio [(A)/(B)] of the component (A) to the component (B) is 0.1 or more and 1,000 or less, and the content of an anionic surfactant is 4% by mass or less.

DETAILED DESCRIPTION OF THE INVENTION

The hair is damaged by the living environment (ultraviolet rays or heat of sunlight), the daily hair-care activities (friction by hair washing or brushing), and the chemical treatment (coloring, perm, etc.). When the damaged hairs rub against each other, a large frictional force is generated on the surface, and entanglement is caused. The "entanglement of hair" is a cause of all of stresses in the hair-care activities, and there was involved such a problem that when the entanglement of hair is once generated, it is difficult to dissociate the entanglement. Although the entanglement of hair is possibly generated during hair washing, during conditioning, after towel drying, or during drying with a hair dryer or the like, according to the research made by the present inventors, it has been noted that when the entanglement of hair is generated at the stage of hair washing, even if a conditioning treatment is subsequently performed, it is difficult to completely dissociate the entanglement. Accordingly, it is preferred that the entanglement of hair can be inhibited or solved during hair washing.

In particular, when performing an action to allow hairs to rub against each other by, for example, towel drying, the hairs which have been dissociated through the conditioning treatment are again strongly entangled in cooperation with friction with the towel. Accordingly, massive time and effort are taken for the action to dissociate the entanglement in addition to drying, and a long time is required for drying.

PTLs 1 and 2 do not disclose inhibition and solution of the entanglement of hair on the occasion of hair washing, in particular, spontaneous dissociation of the entanglement of hair without performing an operation of putting fingers through hair or the like.

The present invention is concerned with a detergent that is favorable in lathering during washing and is able to inhibit and solve the generation of entanglement of a washing object, such as hair and fibers, even during washing and after washing without performing an operation of putting fingers through hair or the like.

The present inventors have found that the aforementioned problem can be solved by a detergent containing a predetermined ampholytic surfactant and/or nonionic surfactant and a quaternary ammonium cation-modified silicone having a predetermined structure in a predetermined proportion.

Specifically, the present invention relates to a detergent containing (A) at least one selected from the group consisting of (A) a carbobetaine type ampholytic surfactant and (A2) a nonionic surfactant, and (B) a quaternary ammonium cation-modified silicone represented by the following general formula (1):

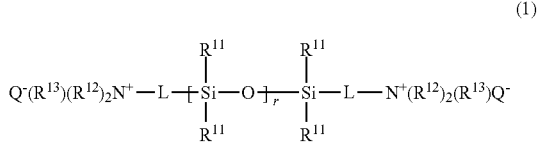

(1)

[in the formula (1), $R^{11}$ represents a hydrocarbon group having 1 or more and 6 or less carbon atoms; $R^{12}$ represents a hydrogen atom, a hydrocarbon group having 1 or more and 20 or less carbon atoms, or an amide bond-containing hydrocarbon group having 1 or more and 20 or less carbon atoms; $R^{13}$ represents a hydrocarbon group having 1 or more and 20 or less carbon atoms, or an amide bond-containing hydrocarbon group having 1 or more and 20 or less carbon atoms; L represents a divalent organic group; $Q^-$ is a counter ion of the quaternary ammonium ion; r represents a number of 2 or more; plural $R^{11}$'s and $R^{12}$'s may be the same as or different from each other; and the bonding order among the structural units within the bracket does not matter, and the bonding form may be a block form or a random form],
wherein,
   a mass ratio [(A)/(B)] of the component (A) to the component (B) is 0.1 or more and 1,000 or less, and the content of an anionic surfactant is 4% by mass or less.

In accordance with the detergent of the present invention, lathering during washing is favorable, and the generation of entanglement of a washing object, such as hair and fibers, even during washing and after washing can be inhibited and solved without performing an operation of putting fingers through hair or the like. For example, in the case where the detergent of the present invention is a hair detergent, the entanglement in hair after washing and towel drying is hardly generated, and therefore, the hair can be dried for a short time, and finish after drying becomes favorable.

[Detergent]

The detergent of the present invention is a detergent containing
   (A) at least one selected from the group consisting of (A1) a carbobetaine type ampholytic surfactant and (A2) a nonionic surfactant, and
   (B) a quaternary ammonium cation-modified silicone represented by the following general formula (1):

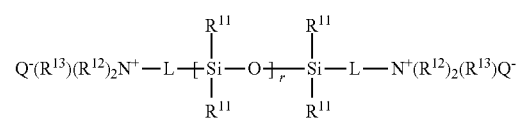

(1)

[in the formula (1), $R^{11}$ represents a hydrocarbon group having 1 or more and 6 or less carbon atoms; $R^{12}$ represents a hydrogen atom, a hydrocarbon group having 1 or more and 20 or less carbon atoms, or an amide bond-containing hydrocarbon group having 1 or more and 20 or less carbon atoms; $R^{13}$ represents a hydrocarbon group having 1 or more and 20 or less carbon atoms, or an amide bond-containing hydrocarbon group having 1 or more and 20 or less carbon atoms; L represents a divalent organic group; $Q^-$ is a counter ion of the quaternary ammonium ion; r represents a number of 2 or more; plural $R^{11}$'s and $R^{12}$'s may be the same as or different from each other; and the bonding order among the structural units within the bracket does not matter, and the bonding form may be a block form or a random form],
wherein,
   a mass ratio [(A)/(B)] of the component (A) to the component (B) is 0.1 or more and 1,000 or less, and the content of an anionic surfactant is 4% by mass or less.

In view of the fact that the detergent of the present invention has the aforementioned constitution, it is favorable in lathering during washing and is able to effectively inhibit and solve the generation of entanglement of a washing object, such as hair and fibers, during washing and even after washing. For example, in the case where the detergent of the present invention is a hair detergent, only by washing the hair with the foregoing hair detergent, the entanglement of hair can be inhibited, and even when an operation of putting fingers through hair or the like to dissociate the hair is not performed, the entanglement of hair can be spontaneously dissociated. The expression "one containing the component (A) and the component (B)" also means "one prepared by blending the component (A) and the component (B)".

The reasons that, because the detergent of the present invention has the aforementioned constitution, the effects of the present invention are exerted are as follows.

In order to reveal such a state that the entanglement of hair or the like is spontaneously dissociated during washing and after washing of hair or fibers, it may be considered to be important to lower a frictional force working on the hair or between the fibers. In a hair detergent, a silicone is generally blended as an active ingredient; however, the present inventors have found that in order that a frictional force working on the hair or between the fibers may be lowered and further, the entanglement of hair or the like may be spontaneously dissociated, it is effective to use the component (B) that is a quaternary ammonium cation-modified silicone having a predetermined structure. The component (B) has a hydrophilic quaternary ammonium cation moiety in the structure thereof, is water-soluble as compared to silicones having high hydrophobicity, is high in hydrophilicity, and is able to readily enter an entangled site with hair or fibers during washing, so that it may be considered that the component (B) acts effectively on hair or fibers, and has a high effect for allowing the entanglement of hair or the like to be spontaneously dissociated. Here, the wording "water-soluble" as referred to in this specification means that the solubility in water at 25° C. is 0.1 g/100 g or more.

On the other hand, in general, the anionic component, such as an anionic surfactant, is blended in a detergent in order to impart detergency; however, since the component (B) is cationic, in the case where the component (B) and an anionic component, such as an anionic surfactant, are coexistent, the component (B) and the anionic component form a complex due to an electrostatic interaction, to cause insolubilization, so that there is a case where the function to remove the entanglement cannot be effectively exhibited.

In the detergent of the present invention, it may be considered that when the component (A) that is the predetermined ampholytic surfactant and/or nonionic surfactant in which an electrostatic interaction with a cation component is considered to hardly occur is used in a predetermined proportion as the surfactant component relative to the component (B), and further, the content of the anionic surfactant is controlled to a predetermined value or less, not only the detergency is imparted, but also the function due to the component (B) is effectively exhibited against a washing object, such as hair and fibers, so that the effects of the present invention can be provided.

When towel drying is performed in a state that the entanglement of hair is dissociated, a contact area between the hair and the towel increases so that the moisture of the hair is quickly absorbed onto the towel. In addition, it may be considered that a contact area between the hair and air increases during drying with a hair dryer or during natural drying, and the moisture in the hair is quickly transpired, so that a drying speed of the hair is improved.

From the viewpoint of effectively obtaining the effects of the present invention, the detergent of the present invention is preferably a hair detergent or a detergent for fibers, and more preferably a hair detergent.

A dosage form of the detergent is not particularly limited, and it is possible to adopt an arbitrary dosage form, for example, a liquid form, a lathering form, a paste form, a cream form, a solid form, or a powder form. For example, in the case of a hair detergent, a liquid form, a paste form or a cream form is preferred, and a liquid form is more preferred.

<Component (A)>

The detergent of the present invention contains, as the component (A), at least one selected from the group consisting of (A1) a carbobetaine type ampholytic surfactant and (A2) a nonionic surfactant. The component (A) is used for the purpose of imparting detergency.

(Carbobetaine Type Ampholytic Surfactant (A1))

Examples of the carbobetaine type ampholytic surfactant that is used as the component (A1) include an alkylbetaine and a fatty acid amidoalkylbetaine. For example, there is exemplified a compound represented by the following general formula (a).

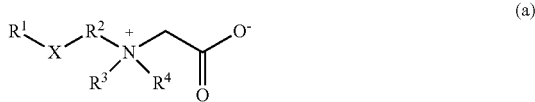

(a)

In the formula (a), $R^1$ represents an alkyl group having 7 or more and 22 or less carbon atoms; $R^2$ represents a single bond or an alkylene group having 1 or more and 6 or less carbon atoms; $R^3$ and $R^4$ each independently represent an alkyl group having 1 or more and 3 or less carbon atoms; and X represents a single bond or —CONH—.

$R^1$ is an alkyl group having 7 or more and 22 or less carbon atoms, and preferably 9 or more and 18 or less carbon atoms. Examples of $R^1$ include a heptyl group, an octyl group, a 2-ethylhexyl group, a nonyl group, a decyl group, a dodecyl group, a lauryl group, a tetradecyl group, a myristyl group, a pentadecyl group, a cetyl group, a heptadecyl group, a stearyl group, a nonadecyl group, an eicosyl group, and a behenyl group. Of these, at least one selected from the group consisting of a decyl group, a dodecyl group, a lauryl group, a tetradecyl group, a myristyl group, a pentadecyl group, a cetyl group, a heptadecyl group, and a stearyl group is preferred.

$R^2$ is a single bond or an alkylene group having 1 or more and 6 or less carbon atoms, preferably an alkylene group 1 or more and 6 or less carbon atoms, and more preferably an alkylene group having 2 or more and 4 or less carbon atoms.

In $R^3$ and $R^4$, examples of the alkyl group having 1 or more and 3 or less carbon atoms include a methyl group, an ethyl group, a n-propyl group, and an isopropyl group, with a methyl group being preferred. More preferably, both $R^3$ and $R^4$ are a methyl group. X is a single bond or —CONH—, with —CONH— being preferred.

Among the compounds represented by the general formula (a), specific examples of the alkylbetaine include lauryldimethylaminoacetic acid betaine and stearyldimethylaminoacetic acid betaine; and specific examples of the fatty acid amidoalkyl betaine include fatty acid amidopropyl betaines, such as lauric acid amidopropyl betaine [lauramidopropyl betaine], palm kernel oil fatty acid amidopropyl betaine, and coconut oil fatty acid amidopropyl betaine [cocamidopropyl betaine].

Among those mentioned above, from the viewpoint of lathering during washing, the component (A1) is more preferably a fatty acid amidoalkylbetaine having an acyl group having 8 or more and 22 or less carbon atoms, still more preferably a fatty acid amidoalkylbetaine having an acyl group having 8 or more and 18 or less carbon atoms; and yet still more preferably at least one selected from the group consisting of lauric acid amidopropyl betaine [lauramidopropyl betaine] and coconut oil fatty acid amidopropyl betaine [cocamidopropyl betaine].

<Nonionic Surfactant (A2)>

Examples of the nonionic surfactant that is used as the component (A2) include a polyoxyalkylene alkyl ether, a polyoxyalkylene alkenyl ether, a polyoxyalkylene sorbitan fatty acid ester, a polyoxyalkylene fatty acid ester, an alkyl glucoside, an alkyl glyceryl ether, a higher fatty acid sugar ester, a polyglycerin fatty acid ester, a polyoxyethylene hydrogenated castor oil, an alkyl saccharide, an alkylamine oxide, and an alkylamidoamine oxide.

Of these, from the viewpoint of lathering during washing, as the component (A2), at least one selected from the group consisting of a polyoxyalkylene alkyl ether, a polyoxyalkylene alkenyl ether, a polyoxyalkylene sorbitan fatty acid ester, a polyoxyalkylene fatty acid ester, an alkyl glucoside, and an alkyl glyceryl ether is preferred; at least one selected from the group consisting of a polyoxyalkylene alkyl ether, an alkyl glucoside, and an alkyl glyceryl ether is more preferred; and an alkyl glucoside is still more preferred.

The carbon number of each of the alkyl group in the polyoxyalkylene alkyl ether, the alkyl glycoside, the alkyl glyceryl ether, the alkyl saccharide, the alkylamine oxide, and the alkylamidoamine oxide; the alkenyl group in the polyoxyalkylene alkenyl ether; and the fatty acid in the polyoxyalkylene sorbitan fatty acid ester, the polyoxyalkylene fatty acid ester, the higher fatty acid sugar ester, and the polyglycerin fatty acid ester is preferably 8 or more and 22 or less, more preferably 8 or more and 18 or less, and still more preferably 8 or more and 12 or less.

As the polyoxyalkylene alkyl ether, there is exemplified a polyoxyethylene alkyl ether or a polyoxypropylene alkyl ether having an alkyl group having preferably 8 or more and 22 or less carbon atoms, more preferably 8 or more and 18 or less carbon atoms, and still more preferably 8 or more and 12 or less carbon atoms. Specific examples thereof include "EMULGEN 103" (Laureth-3: PEG-3 lauryl ether), "EMULGEN 116" (Laureth-16: PEG-16 lauryl ether), and "KAO SOFCARE GP-1" (PPG-3 caprylyl ether), all of which are manufactured by Kao Corporation.

As the alkyl glucoside, there is exemplified an alkyl glucoside having an alkyl group having preferably 8 or more and 22 or less carbon atoms, more preferably 8 or more and 18 or less carbon atoms, and still more preferably 8 or more and 12 or less carbon atoms. Specific examples thereof include "MYDOL 10" (decyl glucoside), manufactured by Kao Corporation; and "Plantaren 2000 N UP" (decyl glucoside) and "Plantacare 818 UP" (coco glucoside), all of which are manufactured by BASF SE.

As the alkyl glyceryl ether, there is exemplified an alkyl glyceryl ether having an alkyl group having preferably 8 or more and 22 or less carbon atoms, more preferably 8 or more and 18 or less carbon atoms, and still more preferably 8 or more and 12 or less carbon atoms. Specific examples thereof include "PENETOL GE-ID" (isodecyl glyceryl ether), manufactured by Kao Corporation. These may be used alone or in combination of two or more thereof.

As the component (A), one or more of the aforementioned carbobetaine type ampholytic surfactant (A1) and nonionic surfactant (A2) may be used, and the carbobetaine type ampholytic surfactant (A1) and the nonionic surface (A2) may be jointly used. In the case of jointly using the component (A1) and the component (A2), though a mass ratio thereof is not particularly restricted, from the viewpoint of making lathering during washing and inhibition of entanglement of a washing object, such as hair, compatible with each other, a mass ratio [(A1)/(A2)] is preferably 0.05 or more, more preferably 0.1 or more, still more preferably 0.15 or more, yet still more preferably 0.2 or more, and even yet still more preferably 0.25 or more, and from the same viewpoint, it is preferably 10 or less, more preferably 8 or less, and still more preferably 5 or less. A specific range of the mass ratio [(A1)/(A2)] is preferably 0.05 to 10, more preferably 0.1 to 8, still more preferably 0.15 to 8, yet still more preferably 0.2 to 5, and even yet still more preferably 0.25 to 5.

From the viewpoint of lathering during washing and inhibition and solution of entanglement of a washing object, such as hair, and the viewpoint of reduction in entanglement during hair rinsing, easiness of brushing after towel drying, and quick drying properties in the hair detergent, the content of the component (A) in the detergent is preferably 1% by mass or more, more preferably 3% by mass or more, still more preferably 5% by mass or more, and yet still more preferably 8% by mass or more, and from the same viewpoints, it is preferably 30% by mass or less, more preferably 20% by mass or less, and still more preferably 18% by mass or less. A specific range of the component (A) in the detergent is preferably 1 to 30% by mass, more preferably 3 to 20% by mass, still more preferably 5 to 18% by mass, and yet still more preferably 8 to 18% by mass.

<Component (B): Quaternary Ammonium Cation-Modified Silicone Represented by General Formula (1)>

The detergent of the present invention contains, as the component (B), a quaternary ammonium cation-modified silicone represented by the following general formula (1). In view of the fact that the detergent of the present invention contains the component (B), in the washing object, such as hair and fibers, the generation of entanglement can be effectively inhibited and solved owing to the aforementioned mechanism of action even during washing and after washing.

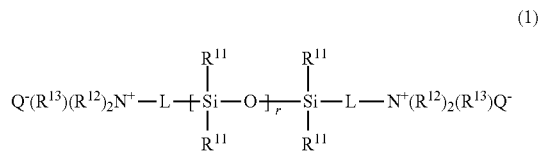

(1)

In the formula (1), $R^{11}$ represents a hydrocarbon group having 1 or more and 6 or less carbon atoms; $R^{12}$ represents a hydrogen atom, a hydrocarbon group having 1 or more and 20 or less carbon atoms, or an amide bond-containing hydrocarbon group having 1 or more and 20 or less carbon atoms; $R^{13}$ represents a hydrocarbon group having 1 or more and 20 or less carbon atoms, or an amide bond-containing hydrocarbon group having 1 or more and 20 or less carbon atoms; L represents a divalent organic group; $Q^-$ is a counter ion of the quaternary ammonium ion; r represents a number of 2 or more; plural $R^{11}$'s and $R^{12}$'s may be the same as or different from each other; and the bonding order among the structural units within the bracket does not matter, and the bonding form may be a block form or a random form.

In the general formula (1), $R^{11}$'s are each independently preferably an alkyl group having 1 or more and 6 or less carbon atoms or a phenyl group, more preferably a methyl group or an ethyl group, and still more preferably a methyl group.

$R^{12}$ is preferably a hydrocarbon group having 1 or more and 20 or less carbon atoms, and more preferably a methyl group.

$R^{13}$ is preferably an amide bond-containing hydrocarbon group having 1 or more and 20 or less carbon atoms, and more preferably —$R^{14}$—NHCO—$R^{15}$.

Here, $R^{14}$ is an alkylene group or an oxyalkylene group each having 1 or more and 18 or less carbon atoms, preferably an alkylene group having 1 or more and 18 or less carbon atoms, and more preferably an alkylene group having 2 or more and 6 or less carbon atoms. $R^{15}$ is an alkyl group having 1 or more and 18 or less carbon atoms, and preferably an alkyl group having 8 or more and 18 or less carbon atoms.

L is preferably $*^1$—$R^{16}$—$CH_2$—CHOH—$CH_2$—$*^2$. Here, $R^{16}$ is preferably an alkylene group having 1 or more and 20 or less carbon atoms or an oxyalkylene group having 1 or more and 20 or less carbon atoms, more preferably an oxyalkylene group having 1 or more and 20 or less carbon atoms, and still more preferably an oxyalkylene group having 2 or more and 6 or less carbon atoms. $*^1$ represents a binding site to the silicon atom, and $*^2$ represents a binding site to the nitrogen atom.

In the general formula (1), r is preferably a number of 2 or more and 200 or less, more preferably a number of 2 or more and 100 or less, still more preferably a number of 10 or more and 100 or less, and yet still more preferably a number of 20 or more and 100 or less.

$Q^-$ represents an anion, such as a halide ion, e.g., a chloride ion and a bromide ion; and an organic acid ion, e.g., an alkyl sulfate ion having 1 or more and 3 or less carbon atoms, an acetate ion, a lactate ion, a benzoate ion, an adipate ion, a formate ion, a malate ion, a citrate ion, and a glycolate ion. Of these, an organic acid ion is preferred, and an acetate ion or a lactate ion is more preferred.

The component (B) is more preferably a quaternary ammonium cation-modified silicone represented by the following general formula (1-1).

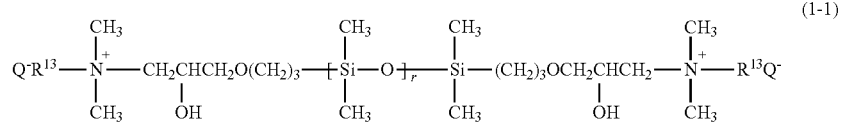

(1-1)

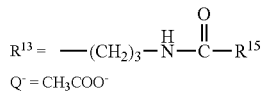

$Q^- = CH_3COO^-$

In the formula (1-1), r is the same as mentioned above; and $R^{15}$ is an alkyl group having 8 or more and 18 or less carbon atoms.

As the quaternary ammonium cation-modified silicone represented by the general formula (1-1), there is exemplified Quaternium-80. Specific examples thereof include "ABIL QUAT 3272" (r=30) and "ABIL QUAT 3474" (r=80), both of which are manufactured by Evonik Industries AG.

In the detergent of the present invention, from the viewpoint of lathering during washing and inhibition and solution of entanglement of a washing object, such as hair, and the viewpoint of reduction in entanglement during hair rinsing, easiness of brushing after towel drying, and quick drying properties in the hair detergent, and the viewpoint of easiness of blending, a mass ratio [(A)/(B)] of the component (A) to the component (B) is 0.1 or more, preferably 1 or more, more preferably 2 or more, still more preferably 5 or more, yet still more preferably 7 or more, and even yet still more preferably 10 or more, and it is 1,000 or less, preferably 500 or less, more preferably 200 or less, still more preferably 100 or less, yet still more preferably 70 or less, and even yet still more preferably 50 or less. A specific range of the mass ratio [(A)/(B)] of the component (A) to the component (B) in the detergent is 0.1 to 1,000, preferably 1 to 1,000, more preferably 2 to 500, still more preferably 5 to 200, yet still more preferably 7 to 100, even yet still more preferably 10 to 70, and even still more preferably 10 to 50.

Although the content of the component (B) in the detergent may be the amount at which the mass ratio [(A)/(B)] is 0.1 or more and 1,000 or less, from the viewpoint of inhibition and solution of entanglement of a washing object, such as hair, and the viewpoint of reduction in entanglement during hair rinsing, easiness of brushing after towel drying, and quick drying properties in the hair detergent, it is preferably 0.01% by mass or more, more preferably 0.05% by mass or more, and still more preferably 0.1% by mass or more, and from the viewpoint of lathering during washing, it is preferably 10% by mass or less, more preferably 7% by mass or less, still more preferably 5% by mass or less, and yet still more preferably 3% by mass or less. A specific range of the content of the component (B) in the detergent is preferably 0.01 to 10% by mass, more preferably 0.01 to 7% by mass, still more preferably 0.01 to 5% by mass, yet still more preferably 0.05 to 5% by mass, even yet still more preferably 0.1 to 5% by mass, and even still more preferably 0.1 to 3% by mass.

<Component (A1'): Ampholytic Surfactant Other than Component (A1)>

For the purpose of lathering during washing and strengthening reduction in entanglement during hair rinsing, easiness of brushing after towel drying, and quick drying properties in the hair detergent, the detergent of the present invention may further contain, as a component (A1'), an ampholytic surfactant other than the component (A1).

Examples of the component (A1') include ampholytic surfactants other than the carbobetaine type, for example, sulfobetaine types, such as an alkylsulfobetaine and an alkylhydroxysulfobetaine; imidazoline-based betaine types; and phosphobetaine types.

Among the sulfobetaine type ampholytic surfactants, examples of the alkylsulfobetaine include an alkylsulfobetaine having an alkyl group having preferably 8 or more and 22 or less carbon atoms, and more preferably 10 or more and 18 or less carbon atoms. Specific examples of the alkylsulfobetaine include lauryldimethylsulfoethyl betaine, lauryldimethylsulfopropyl betaine, myristyldimethylsulfoethyl betaine, myristyldimethylsulfopropyl betaine, stearyldimethylsulfoethyl betaine, stearyldimethylsulfopropyl betaine, and coconut oil fatty acid dimethylsulfopropyl betaine.

As the alkylhydroxysulfobetaine, there is exemplified an alkylhydroxysulfobetaine having an alkyl group having preferably 8 or more and 22 or less carbon atoms, and more preferably 10 or more and 18 or less carbon atoms and having at least one hydroxy group. Specific examples of the alkylhydroxysulfobetaine include lauryldimethylsulfo(hydroxyethyl) betaine, lauryldimethylsulfo(hydroxypropyl) betaine [laurylhydroxysultaine]myristyldimethylsulfo(hydroxyethyl) betaine, myristyldimethylsulfo(hydroxypropyl) betaine, stearyldimethylsulfo(hydroxypropyl) betaine, bis-(2-hydroxy-ethyl)sulfoethyl betaine, and lauryl bis-(2-hydroxy-ethyl)sulfopropyl betaine. Of these, lauryldimethylsulfo(hydroxypropyl) betaine [laurylhydroxysultaine] is preferred.

As the imidazoline-based betaine type ampholytic surfactant, there is exemplified an N-acylaminoethyl-N-2-hydroxyethylaminocarboxylic acid salt. Examples thereof include N-coconut oil fatty acid acyl-N'-carboxymethyl-N'-hydroxyethylethylenediamine [also referred to as sodium cocoamphoacetate or 2-alkyl-N-carboxymethyl-N-hydroxyethylimidazolinium betaine], N-coconut oil fatty acid acyl-N'-carboxyethyl-N'-hydroxyethylethylenediamine [sodium cocoamphopropionate], and sodium N-lauroyl-N'-carboxymethyl-N'-hydroxyethylethylenediamine [sodium lauroamphoacetate].

As the phosphobetaine type ampholytic surfactant, there is exemplified lauryl hydroxyphosphobetaine.

As the component (A1'), one or more of those mentioned above may be used.

Among those mentioned above, the component (A1') is preferably at least one selected from the group consisting of a sulfobetaine type ampholytic surfactant and an imidazoline-based betaine type ampholytic surfactant, more preferably at least one selected from the group consisting of an alkylhydroxysulfobetaine and an imidazoline-based betaine type ampholytic surfactant, and still more preferably at least one selected from the group consisting of lauryldimethylsulfo(hydroxypropyl) betaine [laurylhydroxysultaine] and sodium N-lauroyl-N'-carboxymethyl-N'-hydroxyethylethylenediamine [sodium lauroamphoacetate].

In the case of using the component (A1'), from the viewpoint of lathering during washing, the content of the component (A1') in the detergent is preferably 0.01% by mass or more, more preferably 0.05% by mass or more, still more preferably 0.1% by mass or more, and yet still more preferably 0.3% by mass or more, and from the viewpoint of reduction in entanglement during hair rinsing and easiness of brushing after towel drying in the hair detergent, and easiness of blending, it is preferably 10% by mass or less, more preferably 5% by mass or less, still more preferably 3% by mass or less, yet still more preferably 2% by mass or less, and even yet still more preferably 1.5% by mass or less. A specific range of the content of the component (A1') in the detergent is preferably 0.01 to 10% by mass, more preferably 0.05 to 5% by mass, still more preferably 0.1 to 3% by mass, yet still more preferably 0.3 to 2% by mass, and even yet still more preferably 0.3 to 1.5% by mass.

In the case of using the component (A1'), from the viewpoint of lathering during washing and reduction in entanglement during hair rinsing, easiness of brushing after towel drying, and quick drying properties in the hair detergent, and easiness of blending, a mass ratio [(A)/(A1')] of the component (A) to the component (A1') in the detergent is preferably 0.1 or more, more preferably 0.5 or more, still more preferably 1 or more, yet still more preferably 3 or more, even yet still more preferably 5 or more, and even still more preferably 10 or more, and it is preferably 1,000 or less, more preferably 500 or less, still more preferably 300 or less, yet still more preferably 100 or less, even yet still more preferably 50 or less, and even still more preferably 30 or less.

A specific range of the mass ratio [(A)/(A1')] of the component (A) to the component (A1') in the detergent is preferably 0.1 to 1,000, more preferably 0.5 to 500, still more preferably 1 to 300, yet still more preferably 3 to 100, even yet still more preferably 5 to 50, even still more preferably 5 to 30, and even still more further preferably 10 to 30.

<Component (C): Cationic Surfactant>

From the viewpoint of strengthening reduction in entanglement during hair rinsing, easiness of brushing after towel drying, and quick drying properties in the hair detergent, the detergent of the present invention may further contain, as a component (C), a cationic surfactant.

Examples of the cationic surfactant include (i) an alkyltrimethylammonium salt, (ii) an alkoxyalkyltrimethylammonium salt, (iii) a dialkyldimethylammonium salt, (iv) an alkylamidoalkyltrimethylammonium salt, (v) an alkyldimethylamine and a salt thereof, (vi) an alkoxyalkyldimethylamine and a salt thereof, and (vii) an alkylamidoalkyldimethylamine and a salt thereof.

As the alkyltrimethylammonium salt (i), there is exemplified an alkyltrimethylammonium salt having an alkyl group having preferably 12 or more and 22 or less carbon atoms, and more preferably 16 or more and 20 or less carbon atoms. Specifically, examples thereof include cetyltrimethylammonium chloride (cetrimonium chloride), stearyltrimethylammonium chloride (steartrimonium chloride), and behenyltrimethylammonium chloride.

As the alkoxyalkyltrimethylammonium salt (ii), there is exemplified an alkoxyalkyltrimethylammonium salt having an alkoxy group having preferably 12 or more and 22 or less carbon atoms, and more preferably 16 or more and 20 or less carbon atoms. Specifically, examples thereof include stearoxypropyltrimethylammonium chloride, stearoxyethyltrimethylammonium chloride, and stearoxyhydroxypropyltrimethylammonium chloride.

As the dialkyldimethylammonium salt (iii), there is exemplified a dialkyldimethylammonium salt having an alkyl group having preferably 12 or more and 22 or less carbon atoms, and more preferably 16 or more and 20 or less carbon atoms. Specifically, examples thereof include distearyldimethylammonium chloride.

As the alkylamidoalkyltrimethylammonium salt (iv), there is exemplified an alkylamidoalkyltrimethylammonium salt having an alkyl group having preferably 11 or more and 21 or less carbon atoms, and more preferably 13 or more and 19 or less carbon atoms. Specifically, examples thereof include palmitamidopropyltrimethylammonium chloride (palmitamidopropyltrimonium chloride).

Each of the alkyldimethylamine (v), the alkoxyalkyldimethylamine (vi), and the alkylamidoalkyldimethylamine (vii) reacts with an acid to become a tertiary amine salt and works as a cationic surfactant.

The alkyl group of each of the alkyldimethylamine and its salt (v) and the alkoxyalkyldimethylamine and its salt (vi) is an alkyl group having preferably 12 or more and 22 or less carbon atoms, and more preferably 16 or more and 20 or less carbon atoms.

The alkyl group of the alkylamidoalkyldimethylamine and its salt (vii) is an alkyl group having preferably 11 or more and 21 or less carbon atoms, and more preferably 15 or more and 19 or less carbon atoms.

The amine in each of (v) to (vii) may be previously reacted with an acid to form a salt and blended in the detergent; or it may be blended as the amine as it stands in the detergent, with which is then blended an acid to form a salt in the composition. In consequence, the aforementioned amine and its salt are herein defined as the cationic surfactant. In addition, the content or blending amount thereof is expressed in terms of a mass of the aforementioned amine.

Examples of the salt of amine in each of (v) to (vii) include salts of an organic acid or an inorganic acid. Examples of the organic acid include monocarboxylic acids, such as acetic acid and propionic acid; dicarboxylic acids, such as malonic acid, succinic acid, glutaric acid, adipic acid, maleic acid, fumaric acid, and phthalic acid; polycarboxylic acids, such as polyglutamic acid; hydroxycarboxylic acids, such as glycolic acid, lactic acid, hydroxyacrylic acid, glyceric acid, malic acid, tartaric acid, and citric acid; and acidic amino acids, such as glutamic acid and aspartic acid. Examples of the inorganic acid include hydrochloric acid, sulfuric acid, and phosphoric acid. Of these, an organic acid is preferred, and at least one selected from the group consisting of a dicarboxylic acid, a hydroxycarboxylic acid, and an acidic amino acid is more preferred. As the dicarboxylic acid, at least one selected from the group consisting of maleic acid and succinic acid is more preferred. As the hydroxycarboxylic acid, at least one selected from the group consisting of glycolic acid, lactic acid, and malic acid is more preferred. As the acidic amino acid, glutamic acid is more preferred.

Examples of the alkyldimethylamine and its salt (v) include N,N-dimethylbehenylamine, N,N-dimethylstearylamine, and organic acid salts thereof. Of these, a lactic acid salt of N,N-dimethylbehenylamine, a glycolic acid salt of N,N-dimethylstearylamine, and so on are preferred.

Examples of the alkoxyalkyldimethylamine and its salt (vi) include N,N-dimethyl-3-hexadecyloxypropylamine, N,N-dimethyl-3-octadecyloxypropylamine, and organic acid salts thereof. Of these, N,N-dimethyl-3-hexadecyloxypropylamine or a salt thereof, N,N-dimethyl-3-octadecyloxypropylamine [stearoxypropyldimethylamine] or a salt thereof, and N,N-dimethyl-3-octadecyloxypropylamine or a salt thereof are preferred.

Examples of the alkylamidoalkyldimethylamine and its salt (vii) include N-[3-(dimethylamino)propyl]docosanamide, N-[3-(dimethylamino)propyl]stearamide, and organic acid salts thereof. Of these, a lactic acid salt of N-[3-(dimethylamino)propyl]docosanamide and a glycolic acid salt of N-[3-(dimethylamino)propyl]stearamide are preferred.

The component (C) may be used alone or in combination of two or more thereof.

Among those mentioned above, as the component (C), at least one selected from the group consisting of the alkyltrimethylammonium salt (i), the alkoxyalkyltrimethylammonium salt (ii), the dialkyldimethylammonium salt (iii), the alkyldimethylamine and its salt (v), the alkoxyalkyldimethylamine and its salt (vi), and the alkylamidoalkyldimethylamine and its salt (vii) is preferred, and at least one selected from the group consisting of the alkyltrimethylammonium salt (i) and the alkoxyalkyldimethylamine and its salt (vi) is more preferred.

In the case of using the component (C), from the viewpoint of strengthening reduction in entanglement during hair rinsing, easiness of brushing after towel drying, and quick drying properties in the hair detergent, the content of the compound (C) in the detergent is preferably 0.01% by mass or more, more preferably 0.05% by mass or more, still more preferably 0.1% by mass or more, and yet still more preferably 0.3% by mass or more, and from the viewpoint of lathering during washing and reduction in entanglement during hair rinsing, easiness of brushing after towel drying, and quick drying properties in the hair detergent, and easiness of blending, it is preferably 5% by mass or less, more preferably 4% by mass or less, still more preferably 3% by mass or less, and yet still more preferably 2% by mass or less. A specific range of the content of the component (C) in the detergent is preferably 0.01 to 5% by mass, more preferably 0.05 to 4% by mass, still more preferably 0.1 to 3% by mass, and yet still more preferably 0.3 to 2% by mass.

In the case of using the component (C) in the detergent of the present invention, from the viewpoint of reduction in entanglement during hair rinsing, easiness of brushing after towel drying, and quick drying properties in the hair detergent, and easiness of blending, a mass ratio [(A)/(C)] of the component (A) to the component (C) is preferably 1 or more, more preferably 3 or more, still more preferably 4 or more, yet still more preferably 5 or more, and even yet still more preferably 10 or more, and it is preferably 100 or less, more preferably 75 or less, still more preferably 50 or less, yet still more preferably 30 or less, and even yet still more preferably 20 or less.

A specific range of the mass ratio [(A)/(C)] of the component (A) to the component (C) is preferably 1 to 100, more preferably 3 to 75, still more preferably 4 to 50, yet still more preferably 5 to 30, even yet still more preferably 5 to 20, and even still more preferably 10 to 20.

<Component (D): Cationic Polymer>

From the viewpoint of strengthening reduction in entanglement during hair rinsing in the hair detergent, the detergent of the present invention may further contain, as a component (D), a cationic polymer. In this specification, the "cationic polymer" refers to a water-soluble polymer having a cationic group and having a cationic charge as a whole, and the cationic group refers to a cation group or a group capable of being ionized to become a cation group. Specifically, examples thereof include a primary amino group, a secondary amino group, a tertiary amino group, and a quaternary ammonium group. The component (D) is a cationic polymer other than the component (B) and a component (B') as mentioned later.

Examples of the cationic polymer that is used as the component (D) include a cationized polygalactomannan, such as cationized guar gum, cationized tara gum, and cationized locust bean gum; a cationized cellulose; a cationized hydroxyalkyl cellulose, such as cationized hydroxyethyl cellulose and cationized hydroxypropyl cellulose; a cationic starch; a cationized polyvinyl alcohol; a quaternized dialkylaminoalkyl (meth)acrylic acid salt polymer, such as a vinylpyrrolidone/N,N-dimethylaminoethyl methacrylic acid diethyl sulfate copolymer and an N,N-dimethylaminoethyl methacrylic acid diethyl sulfate/N,N-dimethylacrylamide/dimethacrylic acid polyethylene glycol copolymer; a diallyl quaternary ammonium salt polymer, such as a polydiallyldimethylammonium chloride, a diallyldimethylammonium chloride/acrylic acid copolymer, a diallyldimethylammonium chloride/acrylamide copolymer, and a diallyldimethylammonium chloride/acrylic acid/acrylamide copolymer; a vinylimidazolium trichloride/vinylpyrrolidone copolymer; a vinylpyrrolidone/alkylaminoalkyl (meth)acrylate copolymer; a vinylpyrrolidone/alkylaminoalkyl (meth)acrylate/vinyl caprolactam copolymer; a vinylpyrrolidone/(meth)acrylamide propyl trimethylammonium chloride copolymer; an alkyl acrylamide/(meth)acrylate/alkylaminoalkyl acrylamide/polyethylene glycol (meth)acrylate copolymer; an adipic acid/dimethylaminohydroxypropyl ethylene triamine copolymer; and cationic polymers described in JP 53-139734 A and JP 60-36407 A. These may be used alone or in combination of two or more thereof. Of these, at least one selected from the group consisting of a cationized polygalactomannan, a cationized hydroxyalkyl cellulose, a quaternized dialkylaminoalkyl (meth)acrylic acid salt polymer, and a diallyl quaternary ammonium salt polymer is preferred; and at least one selected from the group consisting of cationized guar gum, a cationized hydroxyalkyl cellulose, and a quaternized dialkylaminoalkyl (meth)acrylic acid salt polymer is more preferred.

As a commercially available cationic polymer that may be used as the component (D), for example, the following may be exemplified.

(Cationized Guar Gum)

JAGUAR Excel, JAGUAR C-17, and JAGUAR C-14-S (all of which are manufactured by Solvay (Novecare)), etc.

(Cationized Tara Gum)

CATINAL CTR-100 (manufactured by Toho Chemical Industry Co., Ltd.), etc.

(Cationized Locust Bean Gum)

CATINAL CLB-100 (manufactured by Toho Chemical Industry Co., Ltd.), etc.

(Cationized Hydroxyethyl Cellulose)

Polyquaternium-10 (o-[2-hydroxy-3-(trimethylammonio)propyl]hydroxyethyl cellulose chloride): for example, UCARE POLYMER JR-30M and UCARE POLYMER JR-400 (all of which are manufactured by The Dow Chemical Company), POIZ C-60H and POIZ C-150L (all of which are manufactured by Kao Corporation), etc.

Polyquaternium-67: SoftCAT (manufactured by The Dow Chemical Company), etc.

(Cationized Hydroxypropyl Cellulose)

SOFCARE C-HP2W (manufactured by Kao Corporation), etc.

(Cationized Polyvinyl Alcohol)

GOHSENX K-434 (manufactured by The Nippon Synthetic Chemical Industry Co., Ltd.), CM318 (manufactured by Kuraray Co., Ltd.), etc.

(Vinylpyrrolidone/N,N-Dimethylaminoethyl Methacrylic Acid Diethyl Sulfate Copolymer)

Polyquaternium-11: GAFQUAT 734 and GAFQUAT 755N (all of which are manufactured by ISP Japan Ltd.), etc.

N,N-Dimethylaminoethyl Methacrylic Acid Diethyl Sulfate/N,N-Dimethylacrylamide/Dimethacrylic Acid Polyethylene Glycol Copolymer Polyquaternium-52: SOFCARE KG-101E and SOFCARE KG-101W-E (all of which are manufactured by Kao Corporation), etc.

(Polydiallyldimethylammonium Chloride)

Polyquaternium-6: MERQUAT 100 (manufactured by The Lubrizol Corporation), etc.
(Diallyldimethylammonium Chloride/Acrylic Acid Copolymer)

Polyquaternium-22: MERQUAT 280 and MERQUAT 295 (all of which are manufactured by The Lubrizol Corporation), etc.
(Diallyldimethylammonium Chloride/Acrylamide Copolymer)

Polyquaternium-7: MERQUAT 550 (manufactured by The Lubrizol Corporation), etc.
(Diallyldimethylammonium Chloride/Acrylic Acid/Acrylamide Copolymer)

Polyquaternium-39: MERQUAT 3331PR (manufactured by The Lubrizol Corporation), etc.

In the case of using the component (D), from the viewpoint of strengthening reduction in entanglement during hair rinsing in the hair detergent, the content of the component (D) in the detergent is preferably 0.001% by mass or more, more preferably 0.005% by mass or more, still more preferably 0.01% by mass or more, yet still more preferably 0.05% by mass or more, even yet still more preferably 0.1% by mass or more, and even still more preferably 0.3% by mass or more, and from the viewpoint of lathering during washing and reduction in entanglement during hair rinsing, easiness of brushing after towel drying, and quick drying properties in the hair detergent, and easiness of blending, it is preferably 10% by mass or less, more preferably 7% by mass or less, still more preferably 5% by mass or less, yet still more preferably 2% by mass or less, and even yet still more preferably 1.5% by mass or less. A specific range of the content of the component (D) in the detergent is preferably 0.001 to 10% by mass, more preferably 0.005 to 7% by mass, still more preferably 0.01 to 5% by mass, yet still more preferably 0.05 to 2% by mass, even yet still more preferably 0.1 to 2% by mass, even still more preferably 0.3 to 2% by mass, and even still more further preferably 0.3 to 1.5% by mass.

In the case of using the component (D) in the detergent of the present invention, from the viewpoint of lathering during washing and reduction in entanglement during hair rinsing, easiness of brushing after towel drying, and quick drying properties in the hair detergent, and easiness of blending, a mass ratio [(A)/(D)] of the component (A) to the component (D) is preferably 0.1 or more, more preferably 0.3 or more, still more preferably 0.5 or more, yet still more preferably 1 or more, even yet still more preferably 2 or more, and even still more preferably 3 or more, and it is preferably 100 or less, more preferably 50 or less, still more preferably 30 or less, yet still more preferably 25 or less, even yet still more preferably 20 or less, even still more preferably 15 or less, even still more further preferably 13 or less, and even yet still more further preferably 10 or less. A specific range of the mass ratio [(A)/(D)] of the component (A) to the component (D) is preferably 0.1 to 100, more preferably 0.3 to 50, still more preferably 0.5 to 30, yet still more preferably 1 to 25, even yet still more preferably 1 to 20, even still more preferably 1 to 15, even still more further preferably 2 to 13, even yet still more further preferably 3 to 13, and more even yet still more further preferably 3 to 10.

<Component (B'): Silicone Other than Component (B)>

From the viewpoint of strengthening reduction in entanglement during hair rinsing in the hair detergent, the detergent of the present invention may further contain, as a component (B'), a silicone other than the component (B).

Examples of the component (B') include at least one selected from the group consisting of an amino-modified silicone, a polyether-modified silicone, an amino polyether-modified silicone, a dimethylpolysiloxane (dimethicone), a methylphenylpolysiloxane, a fatty acid-modified silicone, an alkoxy-modified silicone, and an alkyl-modified silicone. Of these, at least one selected from the group consisting of an amino-modified silicone, an aminopolyether-modified silicone, and a dimethylpolysiloxane is more preferred.

The amino-modified silicone may be any form of an oil, an emulsion, a solution prepared by diluting with a low-viscosity silicone or a liquid paraffin, and so on. The amino-modified silicone is preferably an aminoethylaminopropylsiloxane-dimethylsiloxane copolymer (amodimethicone). Examples of a commercially available product of the amodimethicone include "DOWSIL SM8904" and "DOWSIL CB-1002" (all of which are manufactured by Dow Toray Co., Ltd.); and "KT-0032" and "XF42-B8922" (all of which are manufactured by Momentive Performance Materials Inc.).

The amino polyether-modified silicone is a modified silicone having an amino group and a polyether structure in a main chain or side chain moiety of a polysiloxane, and from the viewpoint of strengthening reduction in entanglement during hair rinsing in the hair detergent, one having a polyoxyalkylene structure is preferred. The carbon number of the alkylene in the polyoxyalkylene structure is preferably 1 or more and 6 or less, and more preferably 2 or more and 4 or less; and the alkylene in the polyoxyalkylene structure is preferably at least one selected from the group consisting of ethylene, propylene, trimethylene, and tetramethylene, and more preferably at least one selected from the group consisting of ethylene and propylene.

Although the amino polyether-modified silicone may be any form of an oil, an emulsion, and so on, it is preferably an oil. Examples of a commercially available product of the amino polyether-modified silicone include "DOWSIL SILSTYLE 104" ((bisisobutyl PEG-14/amodimethicone) copolymer), "DOWSIL SILSTYLE 201" ((bisisobutyl PEG-14/amodimethicone) copolymer), and "DOWSIL SILSTYLE 401" ((bisisobutyl PEG/PPG-20/35/amodimethicone) copolymer), all of which are manufactured by Dow Toray Co., Ltd.; and "ABIL SOFT AF100" (methoxy PEG/PPG-7/3 aminopropyldimethicone), manufactured by Evonik Industries AG.

The dimethylpolysiloxane may be any form of an oil, an emulsion, a solution prepared by diluting a highly polymerized dimethylpolysiloxane with a low-viscosity silicone or a liquid paraffin, and so on.

Examples of a commercially available product of the dimethylpolysiloxane include SH200 Series (such as SH200C Fluid 1CS, SH200C Fluid 2CS, SH200C Fluid 5CS, SH200C Fluid 10CS, SH200C Fluid 20CS, SH200C Fluid 30CS, SH200C Fluid 50CS, SH200C Fluid 100CS, SH200C Fluid 200CS, SH200C Fluid 350CS, SH200C Fluid 500CS, SH200C Fluid 1,000CS, SH200C Fluid 5,000CS, SH200 Fluid 1.5CS, SH200 Fluid 3,000CS, SH200 Fluid 10,000CS, SH200 Fluid 12,500CS, and SH200 Fluid 30,000CS), "DOWSIL BY11-026", "DOWSIL BY22-020", "DOWSIL BY22-029", "DOWSIL BY22-050A", and "DOWSIL BY22-060" (all of which are manufactured by Dow Toray Co., Ltd.); TSF-451 Series (manufactured by Momentive Performance Materials Inc.); and KF-96 Series, KF9008, and KM904 (all of which are manufactured by Shin-Etsu Chemical Co., Ltd.).

In the case of using the component (B'), from the viewpoint of reduction in entanglement during hair rinsing, easiness of brushing after towel drying, and quick drying properties in the hair detergent, the content of the component (B') in the detergent is preferably 0.001% by mass or more, more preferably 0.005% by mass or more, still more preferably 0.01% by mass or more, and yet still more preferably 0.05% by mass or more, and from the viewpoint of lathering during washing and reduction in entanglement during hair rinsing, easiness of brushing after towel drying, and quick drying properties in the hair detergent, and easiness of blending, it is preferably 10% by mass or less, more preferably 7% by mass or less, still more preferably 5% by mass or less, and yet still more preferably 2% by mass or less. A specific range of the content of the component (B') in the detergent is preferably 0.001 to 10% by mass, more preferably 0.005 to 7% by mass, still more preferably 0.01 to 5% by mass, and yet still more preferably 0.05 to 2% by mass.

In the case of using the component (B') in the detergent of the present invention, from the viewpoint of lathering during washing and reduction in entanglement during hair rinsing, easiness of brushing after towel drying, and quick drying properties in the hair detergent, and easiness of blending, a mass ratio [(A)/(B')] of the component (A) to the component (B') is preferably 1 or more, more preferably 3 or more, still more preferably 5 or more, yet still more preferably 10 or more, and even yet still more preferably 30 or more, and it is preferably 500 or less, more preferably 300 or less, still more preferably 200 or less, and yet still more preferably 100 or less.

A specific range of the mass ratio [(A)/(B')] of the component (A) to the component (B') is preferably 1 to 500, more preferably 3 to 300, still more preferably 5 to 200, yet still more preferably 10 to 200, and even still more preferably 30 to 100.

<Organic Acid>

The detergent of the present invention may further contain an organic acid. In view of the fact that the detergent of the present invention contains the organic acid, the entanglement of a washing object, such as hair, can be inhibited and solved, and the reduction in entanglement during haring rinsing, the easiness of brushing after towel drying, and the quick drying properties in the hair detergent can be strengthened. In addition, in the case of using an amine as the cationic surfactant of the component (C), an amine salt can be formed, and a function to regulate the pH of the detergent is provided, too.

Specific examples of the organic acid include the organic acids exemplified in the salt of the amine of the component (C).

From the viewpoint of effectively exhibiting the function of the component (B) and more effectively inhibiting and solving the entanglement of a washing object, such as hair, the carbon number of the organic acid is preferably 2 or more and 10 or less, more preferably 2 or more and 8 or less, and still more preferably 2 or more and 6 or less.

The organic acid is preferably at least one selected from the group consisting of a dicarboxylic acid, a hydroxycarboxylic acid, and an acidic amino acid; more preferably a hydroxycarboxylic acid; still more preferably a hydroxycarboxylic acid having 2 or more and 10 or less carbon atoms; yet still more preferably a hydroxycarboxylic acid having 2 or more and 8 or less carbon atoms; even yet still more preferably a 2-hydroxycarboxylic acid having 2 or more and 6 or less carbon atoms; and even still more preferably at least one selected from the group consisting of lactic acid, citric acid, and malic acid.

From the viewpoint of strengthening inhibition and solution of entanglement of a washing object, such as hair, the viewpoint of strengthening reduction in entanglement during hair rinsing, easiness of brushing after towel drying, and quick drying properties in the hair detergent, and the viewpoint of stably forming the amine salt of the component (C), the content of the organic acid in the detergent is preferably 0.005% by mass or more, more preferably 0.01% by mass or more, still more preferably 0.05% by mass or more, and yet still more preferably 0.1% by mass or more. In addition, from the viewpoint of strengthening lathering during washing and inhibition and solution of entanglement of a washing object, such as hair, the viewpoint of strengthening reduction in entanglement during hair rinsing, easiness of brushing after towel drying, and quick drying properties in the hair detergent, and the viewpoint of easiness of blending, it is preferably 10% by mass or less, more preferably 5% by mass or less, still more preferably 3% by mass or less, and yet still more preferably 2% by mass or less.

A specific range of the content of the organic acid in the detergent is preferably 0.005 to 10% by mass, more preferably 0.01 to 5% by mass, still more preferably 0.05 to 3% by mass, and yet still more preferably 0.1 to 2% by mass.

<Anionic Surfactant>

The detergent of the present invention may further contain an anionic surfactant. Examples of the anionic surfactant include alkylbenzenesulfonic acid salts, alkyl or alkenyl ether sulfuric acid salts, alkyl or alkenyl sulfuric acid salts, alkylsulfonic acid salts, α-olefin sulfonic acid salts, saturated or unsaturated fatty acid salts, alkyl or alkenyl ether carboxylic acid salts, α-sulfo fatty acid salts, N-acylamino acids, phosphoric acid mono- or diesters, and sulfosuccinic acid esters. Of these, one or two or more thereof may be used.

Examples of a counter ion of the anionic group of the anionic surfactant include alkali metal ions, such as a sodium ion and a potassium ion; alkaline earth metal ions, such as a calcium ion and a magnesium ion; an ammonium ion; and alkanol ammoniums having 1 to 3 alkanol groups having 2 or 3 carbon atoms (for example, monoethanolammonium, diethanolammonium, triethanolammonium, and triisopropanolammonium).

Above all, as the anionic surfactant, at least one selected from the group consisting of alkyl ether sulfuric acid salts, alkyl sulfuric acid salts, α-olefin sulfonic acid salts, and alkyl ether carboxylic acid salts is preferred. Examples of the alkyl ether sulfuric acid salt include polyoxyethylene alkyl ether sulfuric acid salts, such as sodium polyoxyethylene lauryl ether sulfate [sodium laureth sulfate] and ammonium polyoxyethylene lauryl ether sulfate [ammonium laureth sulfate], and examples of the alkyl sulfuric acid salt include sodium lauryl sulfate. Examples of the α-olefin sulfonic acid salt include sodium sulfonates of an α-olefin having preferably 8 or more and 22 or less carbon atoms, and more preferably 10 or more and 18 or less carbon atoms. In addition, examples of the alkyl ether carboxylic acid salt include polyoxyethylene alkyl ether acetic acid salts, such as sodium polyoxyethylene lauryl ether acetate [sodium laureth carboxylate].

The anionic surfactant is more preferably at least one selected from the group consisting of an alkyl ether sulfuric acid salt and an α-olefin sulfonic acid salt, and still more preferably at least one selected from the group consisting of a polyoxyethylene alkyl ether sulfuric acid salt and an α-olefin sulfonic acid salt having 8 or more and 22 or less carbon atoms. The polyoxyethylene alkyl ether sulfuric acid salt is preferably ammonium polyoxyethylene lauryl ether sulfate [ammonium laureth sulfate].

However, from the viewpoint of lathering during washing and quick drying properties, the content of the anionic surfactant in the detergent is 5% by mass or less, more preferably 4.5% by mass or less, still more preferably 4% by mass or less, yet still more preferably 3% by mass or less, even yet still more preferably 2% by mass or less, even still more preferably 1.5% by mass or less, and even still more further preferably 1% by mass or less.

<Aqueous Medium>

The detergent of the present invention typically contains an aqueous medium. Examples of the aqueous medium include water; lower alcohols, such as ethanol and isopropanol; and low-molecular diols and triols having 6 or less carbon atoms, such as 1,3-butylene glycol, glycerin, ethylene glycol, and propylene glycol, with water being preferred. Although the content of the aqueous medium in the detergent may be appropriately selected according to the dosage form of the detergent, it is typically in a range of 5 to 99% by mass, and preferably in a range of 30 to 98% by mass.

<Other Component>

In the detergent of the present invention, other component may be appropriately contained or blended within a range where the object of the present invention is not impaired. Examples of the other component include materials that are typically blended in a hair detergent, such as a pH modifier, an antioxidant, an oil agent, an anti-dandruff agent, a vitamin agent, a disinfectant, an anti-inflammatory agent, an antiseptic, a chelating agent, a moisturizer, a pearlescent agent, a ceramide, a fragrance, and a UV absorber.

A production method of the detergent of the present invention is not particularly limited. For example, the detergent of the present invention may be produced by blending the components (A) and (B) and other components to be used, if desired by the method described in the section of Examples and mixing the contents by using a known agitation apparatus or the like.

A use method of the detergent of the present invention is not particularly limited. The entanglement of hair or fibers during washing and after washing can be prevented through a step of washing a washing object, such as hair and fibers, by a known method by using the detergent of the present invention.

Regarding the aforementioned embodiments, the present invention discloses a detergent and a method of preventing entanglement of hair or fibers.

<1>

A detergent containing
(A) at least one selected from the group consisting of (A1) a fatty acid amidoalkylbetaine having an acyl group having 8 or more and 22 or less carbon atoms and (A2) at least one nonionic surfactant selected from the group consisting of a polyoxyalkylene alkyl ether, an alkyl glucoside, and an alkyl glyceryl ether, and
(B) a quaternary ammonium cation-modified silicone represented by the following general formula (1):

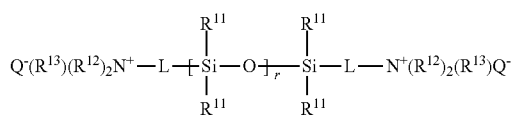

(1)

[in the formula (1), $R^{11}$ represents a hydrocarbon group having 1 or more and 6 or less carbon atoms; $R^{12}$ represents a hydrogen atom, a hydrocarbon group having 1 or more and 20 or less carbon atoms, or an amide bond-containing hydrocarbon group having 1 or more and 20 or less carbon atoms; $R^{13}$ represents a hydrocarbon group having 1 or more and 20 or less carbon atoms, or an amide bond-containing hydrocarbon group having 1 or more and 20 or less carbon atoms; L represents a divalent organic group; $Q^-$ is a counter ion of the quaternary ammonium ion; r represents a number of 2 or more; plural $R^{11}$'s and $R^{12}$'s may be the same as or different from each other; and the bonding order among the structural units within the bracket does not matter, and the bonding form may be a block form or a random form], wherein,
a mass ratio [(A)/(B)] of the component (A) to the component (B) is 2 to 500, and
the content of an anionic surfactant is 4% by mass or less.

<2>

The detergent as set forth in <1>, wherein the content of the component (A) in the detergent is 5 to 18% by mass.

<3>

The detergent as set forth in <1> or <2>, wherein the content of the component (B) in the detergent is 0.1 to 3% by mass.

<4>

The detergent as set forth in any one of <1> to <3>, further containing, as a component (D), a cationic polymer.

<5>

The detergent as set forth in <4>, wherein a mass ratio [(A)/(D)] of the component (A) to the component (D) is 1 to 15.

<6>

The detergent as set forth in any one of <1> to <5>, wherein the content of the anionic surfactant is 3% by mass or less.

<7>

A detergent containing
(A) at least one selected from the group consisting of (A1) a fatty acid amidoalkylbetaine having an acyl group having 8 or more and 22 or less carbon atoms and (A2) at least one nonionic surfactant selected from the group consisting of a polyoxyalkylene alkyl ether, an alkyl glucoside, and an alkyl glyceryl ether, and
(B) a quaternary ammonium cation-modified silicone represented by the following general formula (1):

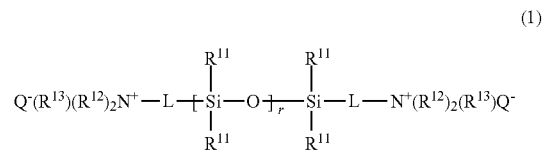

(1)

[in the formula (1), $R^{11}$ represents a hydrocarbon group having 1 or more and 6 or less carbon atoms; $R^{12}$ represents a hydrogen atom, a hydrocarbon group having 1 or more and 20 or less carbon atoms, or an amide bond-containing hydrocarbon group having 1 or more and 20 or less carbon atoms; $R^{13}$ represents a hydrocarbon group having 1 or more and 20 or less carbon atoms, or an amide bond-containing hydrocarbon group having 1 or more and 20 or less carbon atoms; L represents a divalent organic group; Q⁻ is a counter ion of the quaternary ammonium ion; r represents a number of 2 or more; plural R¹¹'s and R¹²'s may be the same as or different from each other; and the bonding order among the structural units within the bracket does not matter, and the bonding form may be a block form or a random form], wherein, a mass ratio [(A)/(B)] of the component (A) to the component (B) is 2 to 500, the content of the component (A) is 5 to 18% by mass, the content of the component (B) is 0.1 to 3% by mass, and the content of an anionic surfactant is 4% by mass or less.

<8>

A detergent containing (A) at least one selected from the group consisting of (A1) a fatty acid amidoalkylbetaine having an acyl group having 8 or more and 22 or less carbon atoms and (A2) at least one nonionic surfactant selected from the group consisting of a polyoxyalkylene alkyl ether, an alkyl glucoside, and an alkyl glyceryl ether, and (B) a quaternary ammonium cation-modified silicone represented by the following general formula (1):

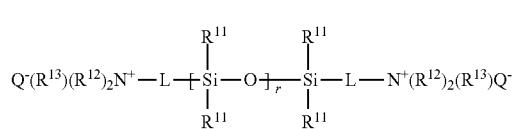

[in the formula (1), R¹¹ represents a hydrocarbon group having 1 or more and 6 or less carbon atoms; R¹² represents a hydrogen atom, a hydrocarbon group having 1 or more and 20 or less carbon atoms, or an amide bond-containing hydrocarbon group having 1 or more and 20 or less carbon atoms; R¹³ represents a hydrocarbon group having 1 or more and 20 or less carbon atoms, or an amide bond-containing hydrocarbon group having 1 or more and 20 or less carbon atoms; L represents a divalent organic group; Q⁻ is a counter ion of the quaternary ammonium ion; r represents a number of 2 or more; plural R¹¹'s and R¹²'s may be the same as or different from each other; and the bonding order among the structural units within the bracket does not matter, and the bonding form may be a block form or a random form], wherein, a mass ratio [(A)/(B)] of the component (A) to the component (B) is 2 to 500, the content of the component (A) is 5 to 18% by mass, the content of the component (B) is 0.1 to 3% by mass, and the content of an anionic surfactant is 3% by mass or less.

<9>

A detergent containing (A) at least one selected from the group consisting of (A1) a fatty acid amidoalkylbetaine having an acyl group having 8 or more and 22 or less carbon atoms and (A2) at least one nonionic surfactant selected from the group consisting of a polyoxyalkylene alkyl ether, an alkyl glucoside, and an alkyl glyceryl ether, and (B) a quaternary ammonium cation-modified silicone represented by the following general formula (1):

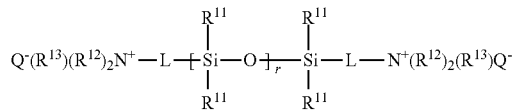

[in the formula (1), R¹¹ represents a hydrocarbon group having 1 or more and 6 or less carbon atoms; R¹² represents a hydrogen atom, a hydrocarbon group having 1 or more and 20 or less carbon atoms, or an amide bond-containing hydrocarbon group having 1 or more and 20 or less carbon atoms; R¹³ represents a hydrocarbon group having 1 or more and 20 or less carbon atoms, or an amide bond-containing hydrocarbon group having 1 or more and 20 or less carbon atoms; L represents a divalent organic group; Q⁻ is a counter ion of the quaternary ammonium ion; r represents a number of 2 or more; plural R¹¹'s and R¹²'s may be the same as or different from each other; and the bonding order among the structural units within the bracket does not matter, and the bonding form may be a block form or a random form], wherein, a mass ratio [(A)/(B)] of the component (A) to the component (B) is 2 to 500, a mass ratio [(A)/(D)] of the component (A) to the component (D) is 1 to 15, the content of the component (A) is 5 to 18% by mass, the content of the component (B) is 0.1 to 3% by mass, and the content of an anionic surfactant is 4% by mass or less.

<10>

The detergent as set forth in any one of <1> to <9>, which is a hair detergent.

<11>

A method for preventing entanglement of hair or fibers, the method including a step of washing hair or fibers by using the detergent as set forth in any one of <1> to <9>.

<12>

Use of the detergent as set forth in any one of <1> to <9> for hair or fibers.

EXAMPLES

The present invention is hereunder described by reference to Examples, but it should be construed that the present invention is not limited to the scope of the Examples. In the present Examples, various measurements and evaluations were performed by the following methods.

(Lathering Evaluation)

A hair bundle of untreated hairs of a Chinese person having a mass of 20 g and a length of 20 cm was damaged through a bleach treatment by a later-mentioned method with the following hair bleach and washed with the following plain shampoo, to obtain a hair bundle for lathering evaluation. This hair bundle for evaluation was thoroughly damped with warm water at 35 to 40° C. and then coated with 1 g of a hair detergent of each of the Examples, followed by washing for 1 minute.

The lathering evaluation was performed by five panelists, and by scoring the lowest as "1" and the highest as "7", respectively, a 7-grade evaluation was performed while defining Comparative Example 1 as a standard score 3. An average grade (rounded off to the first decimal place) of the evaluation by the five panelists was tabulated. The case where the average grade by the five panelists is score 4 or above is considered as passing.
(Evaluation Criteria)
  7: Lathering is very good.
  6: Lathering is better.
  5: Lathering is good.
  4: Lathering is slightly good.
  3: Standards
  2: Lathering is bad.
  1: Lathering is very bad.
[Composition of Plain Shampoo]

| Component | (% by mass) |
|---|---|
| Polyoxyethylene lauryl ether sulfuric acid Na | 11.3 (*1) |
| Coconut oil fatty acid N-methylethanolamide (*2) | 3.0 |
| Citric acid | 0.2 |
| Methyl paraben | 0.3 |
| Purified water | Balance |
| Total | 100.0 |

*1 42.0% by mass as EMAL E-27C (manufactured by Kao Corporation, active ingredient: 27% by mass)
*2 AMINON C-11S (manufactured by Kao Corporation)

[Composition of Hair Bleach]

| Component | (% by mass) |
|---|---|
| Monoethanolamine | 1.5 |
| 28% by mass ammonia water | 4.0 |
| Ammonium bicarbonate | 1.0 |
| 35% by mass hydrogen peroxide water | 8.2 |
| Purified water | Balance |
| Total | 100.0 |

[Bleach Treatment Method]
A hair bundle of untreated hairs of a Chinese person having a mass of 20 g was coated with 20 g of the hair bleach, allowed to stand for 30 minutes, and then thoroughly rinsed with warm water at 35 to 40° C. This operation was repeated four times, thereby preparing a bleach-treated hair bundle.
(Measurement of Combing Load)
The aforementioned hair bundle for lathering evaluation was prepared, thoroughly damped with warm water at 35 to 40° C., and then coated with 1 g of a hair detergent of each of the Examples. The resulting hair bundle was lightly put between palms of both hands and washed for 1 minute while moving the hands so as to rub together. Thereafter, the hair bundle was rinsed with warm water for 30 seconds without allowing the fingers to pass therethrough, thereby obtaining a hair bundle for measurement of combing load.
The aforementioned hair bundle was set on a combing force measuring apparatus (manufactured by Utsunomiya Seiki Co., Ltd., "KOT-0303"), a comb (one in which ten pins having a diameter of 2 mm were linearly arranged at intervals of 4 mm) was allowed to pass through the uppermost part of the hair bundle, and a load (gf) applied when passing the comb through the hair ends was measured. The load was calculated at 200 points of the hair bundle having a length of 20 cm, and a total value of the 200 points in total was designated as "combing load". The smaller the value of combing load, the more excellent the effect for preventing entanglement, and when the combing load is 35,000 gf or less, the effect for preventing entanglement is especially excellent.

(Easiness of Brushing after Towel Drying)
The aforementioned hair bundle for lathering evaluation was prepared, thoroughly damped with warm water at 35 to 40° C., and then coated with 1 g of a hair detergent of each of the Examples. The resulting hair bundle was lightly put between palms of both hands and washed for 1 minute while moving the hands so as to rub together. Thereafter, the hair bundle was rinsed with warm water for 30 seconds. The obtained hair bundle was placed on a towel, and the both surfaces of the hair bundle were covered by the towel and subjected to towel drying so as to rub together, thereby obtaining a hair bundle for brushing evaluation.
The aforementioned hair bundle was set on a combing force measuring apparatus (manufactured by Utsunomiya Seiki Co., Ltd., "KOT-0303"), the root of the hair bundle was put from both sides between two brushes, and an action of simultaneously stroking the brushes towards the hair end was repeated 10 times. A maximum load during one stroke was measured, and the number of strokes required until the load became not more than 400 gf was evaluated. It is meant that as the number of strokes shown in the table is small, after towel drying, the entanglement of hair is small, too, and the brushing is readily performed. The case where the maximum load was not more than 400 gf at stroke during one stroke is taken as "number of strokes: 0".
(Evaluation of Quick Drying Properties)
The aforementioned hair bundle for brushing evaluation was prepared, dried by blowing hot air with a hair dryer (manufactured by Can Co., Ltd., "Sobis TYPE 315", air volume setting: High) at a distance of 5 to 15 cm from the hair bundle while combing fingers, and a time until the wet hair returned to the weight in a dry state was measured (number of measurements: one time). It is meant that as the drying time is short, the quick drying properties are high.

Examples 1 to 24 and Comparative Examples 1 to 3 (Preparation and Evaluation of Hair Detergent)

A hair detergent of each of the Examples was prepared in the following way according to the blending shown in each table and evaluated.
With respect to Examples 1 to 12 and 17 to 24 and Comparative Examples 1 to 3, the components other than the component (B) were uniformly dissolved in an appropriate amount of water, the component (B) (exclusive of Comparative Examples 1 and 2) was added, and the contents were uniformly mixed. With respect to Examples 13 to 16, the components other than the components (B) and (B') were uniformly dissolved in an appropriate amount of water, the component (B) and the component (B') were added, and the contents were uniformly mixed.
Using this hair detergent, the lathering evaluation and the measurement of combing load were carried out by the aforementioned methods.
In addition, with respect to Examples 3, 7, 13 to 20, 23, and 24 and Comparative Examples 1 to 3, the evaluations of easiness of brushing after towel drying and quick drying properties were carried out by the aforementioned methods.
In addition, with respect to Examples 21 and 22, the evaluation of easiness of brushing after towel drying was carried out by the aforementioned method.
The results are shown in Tables 1 to 4. The blending amounts shown in the tables are the active ingredient amount (% by mass) of each of the components.

TABLE 1

|  |  |  |  | Example |  |  |  |  |  |  |  |
|---|---|---|---|---|---|---|---|---|---|---|---|
|  |  |  |  | 1 | 2 | 3 | 4 | 5 | 6 | 7 | 8 |
| Blending (% by mass) | (A1) | Lauramidopropyl betaine | *1 | 5.00 | 10.00 | 10.00 | 10.00 |  |  |  |  |
|  | (A2) | Alkyl glucoside (Decyl glucoside) | *2 |  |  |  |  | 5.00 | 10.00 | 10.00 | 10.00 |
|  | (B) | Quaternium-80 | *3 | 0.10 | 0.10 | 0.30 | 3.00 | 0.10 | 0.10 | 0.30 | 3.00 |
|  | Others | Purified water |  |  |  |  | Balance |  |  |  |  |
| Content of component (A) (% by mass) |  |  |  | 5.00 | 10.00 | 10.00 | 10.00 | 5.00 | 10.00 | 10.00 | 10.00 |
| Mass ratio (A)/(B) |  |  |  | 50.0 | 100 | 33.3 | 3.3 | 50.0 | 100 | 33.3 | 3.3 |
| Mass ratio (A1)/(A2) |  |  |  | — | — | — | — | 0 | 0 | 0 | 0 |
| Evaluation | Lathering |  |  | 4 | 5 | 5 | 4 | 5 | 5 | 5 | 4 |
|  | Combing load (gf) |  |  | 24416 | 20219 | 30413 | 11029 | 23090 | 41290 | 38745 | 6503 |
|  | Easiness of brushing after towel drying (Number of strokes required until the maximum load during one stroke became not more than 400 gf) |  |  | — | — | 1 | — | — | — | 1 | — |
|  | Quick drying properties ((drying time)/sec) |  |  | — | — | 141 | — | — | — | 145 | — |

|  |  |  |  | Example |  |  |  | Comparative Example |  |  |
|---|---|---|---|---|---|---|---|---|---|---|
|  |  |  |  | 9 | 10 | 11 | 12 | 1 | 2 | 3 |
| Blending (% by mass) | (A1) | Lauramidopropyl betaine | *1 | 2.00 | 4.00 | 6.00 | 8.00 | 5.00 |  |  |
|  | (A2) | Alkyl glucoside (Decyl glucoside) | *2 | 8.00 | 6.00 | 4.00 | 2.00 |  | 5.00 |  |
|  | (B) | Quaternium-80 | *3 | 0.30 | 0.30 | 0.30 |  |  |  | 0.10 |
|  | Others | Purified water |  |  |  |  | Balance |  |  |  |
| Content of component (A) (% by mass) |  |  |  | 10.00 | 10.00 | 10.00 | 10.00 | 5.00 | 5.00 | 0.00 |
| Mass ratio (A)/(B) |  |  |  | 33.3 | 33.3 | 33.3 | 33.3 | — | — | 0 |
| Mass ratio (A1)/(A2) |  |  |  | 0.25 | 0.67 | 1.50 | 4.00 | — | 0 | — |
| Evaluation | Lathering |  |  | 6 | 5 | 6 | 6 | 3 | 4 | 1 |
|  | Combing load (gf) |  |  | 42760 | 56683 | 30393 | 24371 | 148025 | 104574 | 36511 |
|  | Easiness of brushing after towel drying (Number of strokes required until the maximum load during one stroke became not more than 400 gf) |  |  | — | — | — | — | 5 | 6 | 2 |
|  | Quick drying properties ((drying time)/sec) |  |  | — | — | — | — | 190 | 237 | 172 |

*1: Manufactured by Kao Corporation, AMPHITOL 20AB (active ingredient: 30%)
*2: Manufactured by Kao Corporation, MYDOL 10 (active ingredient: 40%)
*3: Manufactured by Evonik Industries AG, ABIL QUAT 3272 (active ingredient: 50%)

TABLE 2

|  |  |  |  | Example |  |  |  |
|---|---|---|---|---|---|---|---|
|  |  |  |  | 13 | 14 | 15 | 16 |
| Blending (% by mass) | (A1) | Lauramidopropyl betaine | *1 | 10.00 | 9.00 | 4.00 | 2.00 |
|  | (A2) | Alkyl glucoside (Decyl glucoside) | *2 | 5.00 | 5.00 | 9.00 | 6.00 |
|  |  | Laureth-3 | *3 | 1.00 |  | 1.00 | 1.00 |
|  |  | Laureth-16 | *4 |  | 1.00 |  | 6.00 |
|  |  | PPG-3 caprylyl ether | *5 |  | 0.50 |  | 0.30 |
|  |  | Isodecyl glyceryl ether | *6 | 1.00 |  | 1.00 |  |
|  | (A1') | Laurylhydroxysultaine | *7 |  | 2.00 |  | 1.20 |
|  |  | Sodium lauroamphoacetate | *8 | 1.00 |  | 0.50 |  |
|  | (B) | Quaternium-80 | *9 | 0.30 | 0.30 | 0.30 | 0.30 |
|  | (C) | Stearoxypropyldimethylamine | *10 | 1.10 |  | 1.10 |  |
|  |  | Cetrimonium chloride | *11 |  | 0.20 |  | 0.20 |
|  | (B') | Amino polyether-modified silicone | *12 | 0.30 |  | 0.30 |  |
|  |  | Dimethicone | *13 |  | 0.10 |  | 0.10 |
|  |  | Amodimethicone | *14 |  | 0.10 |  | 0.10 |
|  | Others | Anionic surfactant (Ammonium laureth sulfate) | *15 | 1.00 |  | 1.00 |  |
|  |  | Malic acid | *16 | 0.20 | 0.20 | 0.20 | 0.20 |
|  |  | Antiseptic |  | Moderate amount |  |  |  |
|  |  | Purified water |  | Balance |  |  |  |

TABLE 2-continued

|  |  | Example | | | |
|---|---|---|---|---|---|
|  |  | 13 | 14 | 15 | 16 |
| Content of component (A) (% by mass) | | 17.00 | 15.50 | 15.00 | 15.30 |
| Mass ratio (A)/(B) | | 56.7 | 51.7 | 50.0 | 51.0 |
| Masse ratio (A1)/(A2) | | 1.43 | 1.38 | 0.36 | 0.15 |
| Mass ratio (A)/(A1') | | 17.0 | 7.8 | 30.0 | 12.8 |
| Mass ratio (A)/(C) | | 15.5 | 77.5 | 13.6 | 76.5 |
| Mass ratio (A)/(B') | | 56.7 | 77.5 | 50.0 | 76.5 |
| Evaluation | Lathering | 7 | 7 | 7 | 6 |
|  | Combing load (gf) | 24672 | 43662 | 27180 | 30594 |
|  | Easiness of brushing after towel drying (Number of strokes required until the maximum load during one stroke became not more than 400 gf) | 0 | 1 | 1 | 0 |
|  | Quick drying properties ((drying time)/sec) | 127 | 107 | 95 | 105 |

*1: Manufactured by Kao Corporation, AMPHITOL 20AB (active ingredient: 30%)
*2: Manufactured by Kao Corporation, MYDOL 10 (active ingredient: 40%)
*3: Manufactured by Kao Corporation, EMULGEN 103
*4: Manufactured by Kao Corporation, EMULGEN 116
*5: Manufactured by Kao Corporation, KAO SOFCARE GP-1
*6: Manufactured by Kao Corporation, PENETOL GE-ID
*7: Manufactured by Kao Corporation, AMPHITOL 20HD (active ingredient: 30%)
*8: Manufactured by Kao Corporation, AMPHITOL 20YB (active ingredient: 40%)
*9: Manufactured by Evonik Industries AG, ABIL QLTAT 3272 (active ingredient: 50%)
*10: Manufactured by Kao Corporation, FARMIN DM E-80
*11: Manufactured by Kao Corporation, QUARTAMIN 60W
*12: Manufactured by Dow Toray Co., Ltd., DOWSIL SILSTYLE 201
*13: Manufactured by Dow Toray Co., Ltd., DOWSIL BY22-029 (active ingredient: 50%)
*14: Manufactured by Momentive Performance Materials Tnc., KT-0032 (active ingredient: 40%)
*15: Manufactured by Kao Corporation, EMAL 170S-A (active ingredient: 70%)
*16: Manufactured by Fuse Chemical Co., Ltd., liquid malic acid (active ingredient: 50%)

TABLE 3

|  |  |  |  | Example | | |
|---|---|---|---|---|---|---|
|  |  |  |  | 17 | 18 | 19 |
| Blending (% by mass) | (A1) | Cocamidopropyl betaine | *1 | 3.60 | 3.60 | 3.60 |
|  | (A2) | Decyl glucoside | *2 | 2.75 | 2.75 | 2.75 |
|  |  | Coco glucoside | *3 | 2.75 | 2.75 | 2.75 |
|  | (B) | Quaternium-80 | *4 | 0.60 | 0.60 | 0.45 |
|  | (C) | Stear oxypropyl dimethyl amine | *5 | 0.70 | 0.50 | 0.50 |
|  | (D) | Guar hydroxypropyltrimonium chloride | *6 | 0.30 | 0.30 | 0.30 |
|  |  | Polyquaternium-52 | *7 | 0.20 | 0.20 | 0.20 |
|  |  | Polyquaternium-10 | *8 | 0.20 | 0.20 | 0.20 |
|  |  | Polyquaternium-7 | *9 |  | 0.10 | 0.10 |
|  | Others | Ammonium laureth sulfate | *10 | 2.00 |  |  |
|  |  | Sodium C14-16-olefin sulfate | *11 |  | 4.00 | 4.00 |
|  |  | Citric acid | *12 | 0.30 | 0.30 | 0.30 |
|  |  | Lactic acid | *13 | 0.16 | 0.16 | 0.16 |
|  |  | Antiseptic |  | Moderate amount | | |
|  |  | Purified water |  | Balance | | |
| Content of component (A) (% by mass) | | | | 9.10 | 9.10 | 9.10 |
| Mass ratio (A)/(B) | | | | 15.2 | 15.2 | 20.2 |
| Masse ratio (A1)/(A2) | | | | 0.65 | 0.65 | 0.65 |
| Mass ratio (A)/(C) | | | | 13.0 | 18.2 | 18.2 |
| Mass ratio (A)/(D) | | | | 6.5 | 7.6 | 7.6 |

TABLE 3-continued

|  |  | Example | | |
|---|---|---|---|---|
|  |  | 17 | 18 | 19 |
| Evaluation | Lathering | 7 | 7 | 7 |
|  | Combing load (gf) | 10375 | 7726 | 6746 |
|  | Easiness of brushing after towel drying (Number of strokes required until the maximum load during one stroke became not more than 400 gf) | 0 | 0 | 0 |
|  | Quick drying properties ((drying time)/sec) | 98 | 108 | 103 |

*1: Manufactured by Evonik Industries AG, TEGO BETAIN F KB 5 (active ingredient: 30%)
*2: Manufactured by BASF SE, Flantaren 2000 N UP (active ingredient/50%)
*3: Manufactured by BASF SE, Plantacaro 818 UP (active ingredient: 50%)
*4: Manufactured by Evonik Industries AG, ABIL QUAT 3272 (active ingredient: 50%)
*5: Manufactured by Kao Corporation, FARMIN DM E-80
*6: Manufactured by, Solvay S.A., Jaguar C-17
*7: Manufactured by, Kao Corporation, SOFCARE KG-101E (active ingredient/ 40%)
*8: Manufactured by The Dow Chemical Company, UCARE POLYMER JR-30M
*9: Manufactured by The Lubrizol Corporation, MERQUAT 550
*10: Manufactured by Kao Corporation, EMAL 270D (active ingredient: 70%)
*11: Manufactured by Stepan Company, Bio-Terge AS-40 (active ingredient: 40%)
*12: Manufactured by Calvary Industries, Inc., Citric Acid (50%) (active ingredient: 50%)
*13: Manufactured by PURAC Thailand Ltd., Purac Bioquimica PURAC HiPure 90 (active ingredient: 90%)

TABLE 4

|  |  |  |  | Example | | | | |
|---|---|---|---|---|---|---|---|---|
|  |  |  |  | 20 | 21 | 22 | 23 | 24 |
| Blending (% by mass) | (A1) | Lauramidopropyl betaine | *1 | 3.60 | 3.60 | 3.60 | 3.60 | 3.60 |
|  | (A2) | Alkyl glucoside (Decyl glucoside) | *2 | 2.75 | 2.75 | 2.75 | 2.75 | 2.75 |
|  |  | Lauryl glucoside | *3 | 2.75 | 2.75 | 2.75 | 2.75 | 2.75 |
|  | (B) | Quaternium-80 | *4 | 0.50 | 0.50 | 0.50 | 0.50 | 0.50 |
|  | (D) | Guar hydroxypropyltrimonium chloride | *5 | 0.30 | 0.30 | 0.10 | 0.10 | 0.10 |
|  |  | Polyquaternium-52 | *6 | 0.30 | 0.20 | 0.20 | 0.20 | 0.10 |
|  |  | Polyquaternium-10 | *7 | 0.30 | 0.20 | 0.20 | 0.10 | 0.10 |
|  |  | Polyquaternium-7 | *8 | 0.10 | 0.10 | 0.10 | 0.10 | 0.10 |
|  | Others | Sodium C14-16-olefin sulfate | *9 | 4.00 | 4.00 | 4.00 | 4.00 | 4.00 |
|  |  | Citric acid | *10 | 0.30 | 0.30 | 0.30 | 0.30 | 0.30 |
|  |  | Lactic acid | *11 | 0.16 | 0.16 | 0.16 | 0.16 | 0.16 |
|  |  | Antiseptic |  | Moderate amount | | | | |
|  |  | Purified water |  | Balance | | | | |
| Content of component (A) (% by mass) |  |  |  | 9.10 | 9.10 | 9.10 | 9.10 | 9.10 |
| Mass ratio (A)/(B) |  |  |  | 18.2 | 18.2 | 18.2 | 18.2 | 18.2 |
| Masse ratio (A1)/(A2) |  |  |  | 0.65 | 0.65 | 0.65 | 0.65 | 0.65 |
| Mass ratio (A)/(D) |  |  |  | 9.1 | 11.4 | 15.2 | 18.2 | 22.8 |
| Evaluation | Lathering |  |  | 6 | 6 | 6 | 6 | 5 |
|  | Combing load (gf) |  |  | 10807 | 13279 | 18209 | 13324 | 22714 |
|  | Easiness of brushing after towel drying (Number of strokes required until the maximum load during one stroke became not more than 400 gf) |  |  | 0 | 0 | 0 | 0 | 1 |
|  | Quick drying properties ((drying time)/sec) |  |  | 88 | — | — | 117 | 137 |

*1- Manufactured by Kao Corporation, AMPHITOL· 20AB (active ingredient- 30%)
*2: Manufactured by Kao Corporation, MYDOL 10 (active ingredient: 40%)
*3: Manufactured by Kao Corporation, MYDOL 12 (active ingredient: 40%)
*4: Manufactured by Evonik Industries AG, ABIL QUAT 3272 (active ingredient: 50%)
*5: Manufactured by, Solvay S.A., Jaguar C-14-S
*6: Manufactured by, Kao Corporation, SOECARE KG-101W-E (active ingredient: 2.4%)
*7: Manufactured by Kao Corporation, POIZ C-150L
*8: Manufactured by The Lubrizol Corporation, MERQUAT 550
*9: Manufactured by Stepan Company, Bio-Terge AS-40 (active ingredient: 40%)
*10: Manufactured by Calvary Industries, Inc., Citric Acid (50%) (active ingredient: 50%)
*11: Manufactured by PURAC Thailand Ltd., Purac Bioquimica PURAC HiPure 90 (active ingredient: 90%)

INDUSTRIAL APPLICABILITY

In accordance with the detergent of the present invention, lathering during washing is favorable, and the generation of entanglement of a washing object, such as hair and fibers, even during washing and after washing can be inhibited and solved without performing an operation of putting fingers through hair or the like. For example, in the case where the detergent of the present invention is a hair detergent, the entanglement in hair after washing and towel drying is hardly generated, and therefore, the hair can be dried for a short time, and finish after drying becomes favorable.

The invention claimed is:

1. A detergent comprising:
   (A) from 8 to 18% by mass of at least one surfactant selected from the group consisting of;
   (A1) a betaine surfactant selected from the group consisting of lauramidopropyl betaine and cocoamidopropyl betaine; and
   (A2) a nonionic surfactant selected from the group consisting of a polyoxyalkylene alkyl ether having an alkyl group having 8 or more and 12 or less carbon atoms, an alkyl glucoside having an alkyl group having 8 or more and 12 or less carbon atoms, and an alkyl glyceryl ether having an alkyl group having 8 or more and 12 or less carbon atoms;
   B) quaternium 80;
   C) from 0.05% to 2% by mass of an amino polyether-modified silicone;
   D) a cationic surfactant selected from the group consisting of an alkyltrimethylammonium salt having an alkyl group having 16 or more and 20 or less carbon atoms; and an alkoxyalkyldimethylamine having an alkyl group having 16 or more and 20 or less carbon atoms or a salt thereof, and
   E) from greater than zero up to 4% of an anionic surfactant;
   wherein:
   i) a mass ratio [A/B] of the component (A) to the component (B) is 7 or more and 100 or less;
   ii) a mass ratio [A/D] of the component (A) to the component (D) is 10 or more and 50 or less.

2. The detergent according to claim 1 further comprising an ampholytic surfactant other than component A1.

3. The detergent according to claim 1 further comprising a component (F) cationic polymer.

4. The detergent according to claim 3, wherein a mass ratio [A/F] of the component (A) to the component (F) is one or more and 15 or less.

5. The detergent according to claim 1, which is a hair detergent.

6. The detergent according to claim 1, wherein the mass ratio [(A)/(B)] of the component (A) to the component (B) is 10 or more and 70 or less.

7. A method for preventing entanglement of hair or fibers, the method comprising washing hair or fibers with the detergent of claim 1.

8. The detergent according to claim 1, wherein a mass ratio [A/D] of the component (A) to the component (D) is 10 or more and 30 or less.

9. The detergent according to claim 8, wherein a mass ratio [A/D] of the component (A) to the component (D) is 10 or more and 18.2 or less.

10. The detergent according to claim 1, wherein component (A) comprises both (A1) the betaine surfactant and (A2) the nonionic surfactant.

11. The detergent according to claim 1, wherein the detergent has a combing load of 35,000 gf or less.

* * * * *